(12) United States Patent
Ten Kate et al.

(10) Patent No.: US 9,773,397 B2
(45) Date of Patent: Sep. 26, 2017

(54) METHOD FOR DETECTING FALLS AND A FALL DETECTION SYSTEM

(71) Applicant: KONINKLIJKE PHILIPS N.V., Eindhoven (NL)

(72) Inventors: Warner Rudolph Theophile Ten Kate, Waalre (NL); Patrick Kechichian, Eindoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 14/914,413

(22) PCT Filed: Aug. 8, 2014

(86) PCT No.: PCT/EP2014/067071
§ 371 (c)(1),
(2) Date: Feb. 25, 2016

(87) PCT Pub. No.: WO2015/028283
PCT Pub. Date: Mar. 5, 2015

(65) Prior Publication Data
US 2016/0203692 A1     Jul. 14, 2016

(30) Foreign Application Priority Data
Aug. 26, 2013  (EP) .................................. 13181710

(51) Int. Cl.
*G08B 23/00* (2006.01)
*G08B 21/04* (2006.01)
(Continued)

(52) U.S. Cl.
CPC ........ *G08B 21/0446* (2013.01); *A61B 5/1117* (2013.01); *A61B 5/681* (2013.01);
(Continued)

(58) Field of Classification Search
CPC combination set(s) only.
See application file for complete search history.

(56) References Cited

U.S. PATENT DOCUMENTS

| | | |
|---|---|---|
| 2009/0254003 A1 | 10/2009 | Buckman |
| 2009/0322548 A1 | 12/2009 | Gottlieb |

(Continued)

FOREIGN PATENT DOCUMENTS

| | | |
|---|---|---|
| CN | 102982653 A | 3/2013 |
| EP | 2549228 A1 | 1/2013 |

(Continued)

OTHER PUBLICATIONS

Harmo et al: "Activity Monitoring:Review of the State-of-The-Art of Activity Monitoring of Elderly People for Assisting Independent Living"; Automation and Systems Technology Department, Aalto University, Sep. 22, 2011, pp. 1-35.

(Continued)

*Primary Examiner* — Travis Hunnings (57) ABSTRACT

There is provided a fall detection system comprising a user device configured to be worn or carried by a user, the user device comprising a proximity sensor for measuring the proximity of the user device to the ground or a floor; and a movement sensor for measuring the movements of the user; the fall detection system further comprising a processing unit configured to process the measurements from the movement sensor to detect a potential fall; activate the proximity sensor if a potential fall is detected; and process the measurements from the proximity sensor to determine if the user has fallen.

15 Claims, 7 Drawing Sheets

(51) Int. Cl.
  *A61B 5/11*  (2006.01)
  *A61B 5/00*  (2006.01)

(52) U.S. Cl.
  CPC ............ *A61B 5/746* (2013.01); *G08B 21/043* (2013.01); *G08B 21/0492* (2013.01); *A61B 2560/04* (2013.01); *A61B 2562/0219* (2013.01); *A61B 2562/0247* (2013.01); *A61B 2562/0257* (2013.01)

(56) References Cited

U.S. PATENT DOCUMENTS

2012/0059284 A1  3/2012 Eschler et al.
2013/0312168 A1* 11/2013 Raanan .............. A41D 13/0506
                  2/465

FOREIGN PATENT DOCUMENTS

| | | |
|---|---|---|
| JP | 2000317002 A | 11/2000 |
| WO | 2004114245 A1 | 12/2004 |
| WO | 2009138941 A1 | 11/2009 |
| WO | 2012104833 A2 | 8/2012 |

OTHER PUBLICATIONS

Today's Hospitalist: "Ultrasound System Helps Detect Patient Falls"; May 2008, Downloaded From http://www.todayshospitalist.com/?b=articles_read&cnt=562 on Jun. 6, 2013, 2 page document.

* cited by examiner

METHOD FOR DETECTING FALLS AND A FALL DETECTION SYSTEM

CROSS-REFERENCE TO PRIOR APPLICATIONS

This application is the U.S. National Phase application under 35 U.S.C. §371 of International Application No. PCT/EP2014/067071, filed on Aug. 8, 2014, which claims the benefit of European Patent Application No. 13181710.8 filed on Aug. 26, 2013. These applications are hereby incorporated by reference in their entirety herein.

TECHNICAL FIELD OF THE INVENTION

The invention relates to a method for detecting falls by a user and a fall detection system implementing the same, and in particular relates to a method for detecting falls and a fall detection system that provides increased fall detection reliability.

BACKGROUND TO THE INVENTION

Falls affect millions of people each year and result in significant injuries, particularly among the elderly. In fact, it has been estimated that falls are one of the top three causes of death in elderly people. A fall is defined as a sudden, uncontrolled and unintentional downward displacement of the body to the ground, followed by an impact, after which the body stays down on the ground.

PERS is a system in which help can be assured. By means of Personal Help Buttons (PHBs) the user can push the button to summon help in an emergency. A majority of calls are because the user has fallen. Also, if the user suffers a severe fall (for example by which they get confused or even worse if they are knocked unconscious), the user might be unable to push the button, which might mean that help doesn't arrive for a significant period of time, particularly if the user lives alone. The consequences of a fall can become more severe if the user stays lying for a long time.

Fall detection systems are also available that process the output of one or more movement sensors to determine if the user has suffered a fall. Most existing body-worn fall detection systems make use of an accelerometer (usually an accelerometer that measures acceleration in three dimensions) and they are configured to infer the occurrence of a fall by processing the time series generated by the accelerometer. Some fall detection systems can also include an air pressure sensor, for example as described in WO 2004/114245, for measuring the height, height change or absolute altitude of the fall detection system. On detecting a fall, an alarm is triggered by the fall detection system.

In general, a fall detector tests on features like impact, orientation, orientation change, height change, vertical velocity, and alike. Reliable detection results when the set of computed values for these features is different for falls than for other movements that are not a fall.

Some fall detection systems are designed to be worn as a pendant around the neck of the user, whereas others are designed to be worn on or at the torso (e.g. waist, on a waist belt or in a pocket) or on the limbs of the user, for example at the wrist. However, the wrist is capable of complex movement patterns and has a large range of movement shapes/forms/types, and is also susceptible to non-fall related impacts in which the hand, wrist or arm strikes an object, e.g. furniture or a door frame, during normal movement by the user, which means that existing fall detection methods based on analysing measurements from an accelerometer do not provide a sufficiently high detection rate while minimising the number of false alarms for this type of fall detection system.

Therefore there is a need for a method for detecting falls and a fall detection system that provides increased fall detection reliability, particularly a fall detection system that is worn on the wrist.

SUMMARY OF THE INVENTION

According to a first aspect of the invention, there is provided a fall detection system comprising a user device configured to be worn or carried by a user, the user device comprising: a proximity sensor for measuring the proximity of the user device to the ground or a floor; and a movement sensor for measuring the movements of the user; the fall detection system further comprising a processing unit configured to process the measurements from the movement sensor to detect a potential fall; activate the proximity sensor if a potential fall is detected; and process the measurements from the proximity sensor to determine if the user has fallen.

In preferred embodiments, the proximity sensor is configured to emit ultrasound or light pulses to measure the distance to the ground or a floor.

In preferred embodiments, the movement sensor includes an accelerometer and/or air pressure sensor.

In some embodiments, the processing unit is configured to process the measurements to detect if a potential fall has occurred by processing the measurements to determine a change in height and/or the magnitude of an impact, and to detect a potential fall if the change in height is greater than a first threshold value and/or the magnitude of the impact is greater than a second threshold value.

In preferred embodiments, the processing unit is configured to process the measurements from the proximity sensor and the measurements from the movement sensor to determine if the user has fallen.

In some embodiments, the user device comprises a plurality of proximity sensors that are distributed in different orientations around the user device.

In some embodiments, the processing unit is configured to activate each of the plurality of proximity sensors if a potential fall is detected.

In other embodiments, the processing unit is configured to, on detection of a potential fall, process the measurements from the movement sensor to determine the orientation of the user device, determine which of the plurality of proximity sensors is facing downwards from the determined orientation, and activate the proximity sensor that is determined to be facing downwards.

In some embodiments, each proximity sensor has an associated orientation sensor for determining the orientation of the proximity sensor, and the processing unit is configured to measure the orientation of each proximity sensor using the orientation sensors, and to determine the direction in which each proximity sensor is facing from the measured orientations.

In some embodiments, the user device comprises a plurality of proximity sensors arranged to face in generally the same direction to form an array, and the processing unit is configured to operate the array of proximity sensors together to enable the width of the viewing direction of the array to be changed and/or to enable the direction of a beam formed by the array to be varied or steered.

In some embodiments, the processing unit is configured to, on detection of a potential fall, process the measurements from the movement sensor to determine the orientation of the user device, and to operate the array of proximity sensors together to direct a beam formed by the array downwards according to the determined orientation of the user device.

In some embodiments, the processing unit is configured to control the array to measure the distance to an object in different directions, and to process the distance measurements in different directions to determine the extent or extendedness of the object.

In some embodiments, the processing unit is configured to control the array to measure the distance to an object in different directions, and to determine the extent or extendedness of the object from the strength of the received echo as a function of the relative phase of the beam.

In some embodiments, the processing unit is configured to determine whether the distance measured by the array of proximity sensors is a distance to the ground, the floor or another object from the determined extent or extendedness of the object.

In some embodiments, the processing unit is configured to use the result of the processing to determine whether the distance measured by the object is to the ground, the floor or another object in the processing of the measurements from the proximity sensor and the measurements from the movement sensor to determine if the user has fallen.

In some embodiments, the processing unit is further configured to control the array to measure the distance to different parts of the body of the user, and to determine the posture of the user from the measured distances.

In some embodiments, the processing unit is further configured to determine the relative strength of an echo or reflection of energy emitted by the proximity sensor and to determine whether the reflecting surface is hard or soft and/or the reliability of the measurement of the proximity of the user device to the ground or a floor.

In preferred embodiments, the user device comprises the processing unit. In alternative embodiments, the fall detection system further comprises a base unit that is configured to communicate wirelessly with the user device, the base unit comprising the processing unit.

According to a second aspect, there is provided a method for detecting falls, the method comprising measuring the movements of a user using a movement sensor; processing the measurements from the movement sensor to detect a potential fall; if a potential fall is detected, activate a proximity sensor that measures the proximity of the user device to the ground or a floor; and processing the measurements from the proximity sensor to determine if the user has fallen.

In some embodiments, the step of processing the measurements to detect if a potential fall has occurred comprises processing the measurements to determine a change in height and/or the magnitude of an impact, and detecting a potential fall if the change in height is greater than a first threshold value and/or the magnitude of the impact is greater than a second threshold value.

In preferred embodiments, the step of processing the measurements to determine if the user has fallen comprises processing the measurements from the proximity sensor and the measurements from the movement sensor to determine if the user has fallen.

In some embodiments, there are a plurality of proximity sensors distributed in different orientations around a user device. In those embodiments, the step of activating a proximity sensor comprises activating each of the plurality of proximity sensors if a potential fall is detected. In alternative embodiments, on detecting a potential fall, the method further comprises the step of processing the measurements from the movement sensor to determine the orientation of the user device, and determining which of the plurality of proximity sensors is facing downwards from the determined orientation, and the step of activating comprises activating the proximity sensor that is determined to be facing downwards.

In some embodiments, each proximity sensor has an associated orientation sensor, and the step of determining which of the plurality of proximity sensors is facing downwards comprises using the measurements from each associated orientation sensor to determine which proximity sensor is facing downwards.

In some embodiments, the user device comprises a plurality of proximity sensors arranged to face in generally the same direction to form an array, and the step of activating the proximity sensor comprises operating the array of proximity sensors together to enable the width of the viewing direction of the array to be changed and/or to enable the direction of a beam formed by the array to be varied or steered.

In some embodiments, the method comprises a step of processing the measurements from the movement sensor to determine the orientation of the user device, and the step of activating the proximity sensor comprises operating the array of proximity sensors together to direct a beam formed by the array downwards according to the determined orientation of the user device.

In some embodiments, the step of activating the proximity sensor comprises controlling the array to measure the distance to an object in different directions, and the method further comprises a step of processing the distance measurements in different directions to determine the extent or extendedness of the object.

In some embodiments, the step of activating the proximity sensor comprises controlling the array to measure the distance to an object in different directions, and the method further comprises a step of determining the extent or extendedness of the object from the strength of the received echo as a function of the relative phase of the beam.

In some embodiments, the method further comprises a step of determining whether the distance measured by the array of proximity sensors is a distance to the ground, the floor or another object from the determined extent or extendedness of the object.

In some embodiments, the method further comprises using the result of the processing to determine whether the distance measured by the object is to the ground, the floor or another object in the processing of the measurements from the proximity sensor and the measurements from the movement sensor to determine if the user has fallen.

In some embodiments, the step of activating the proximity sensor comprises controlling the array to measure the distance to different parts of the body of the user, and the method further comprises a step of determining the posture of the user from the measured distances.

In some embodiments, the method further comprises a step of determining the relative strength of an echo or reflection of energy emitted by the proximity sensor and determining whether the reflecting surface is hard or soft and/or the reliability of the measurement of the proximity of the user device to the ground or a floor.

According to the third aspect, there is provided a computer program product having computer readable code embodied therein, the computer readable code being configured such that, on execution by a suitable computer or processing unit, the computer or processing unit performs any of the methods described above.

According to a fourth aspect of the invention, there is provided a method for detecting falls using a fall detection system, the method comprising measuring the movements of a user using a movement sensor; determining the orientation of a user-worn device of the fall detection system; determining which of a plurality of proximity sensors in the user device is facing downwards from the determined orientation, the plurality of proximity sensors being distributed in different orientations around a user device; using one or more proximity sensors that are determined to be facing downwards to measure the proximity of the user device to the ground or a floor; and processing the measurements from the proximity sensor and the measurements from the movement sensor to determine if the user has fallen.

In some embodiments of the fourth aspect, a plurality of proximity sensors are arranged in an array, and the step of using comprises controlling the plurality of proximity sensors to direct a beam formed by the array generally vertically downwards according to the determined orientation.

According to a fifth aspect of the invention, there is provided a fall detection system comprising a user device configured to be worn or carried by a user, the user device comprising: a plurality of proximity sensors for measuring the proximity of the user device to the ground or a floor distributed in different orientations around the user device; and a movement sensor for measuring the movements of the user; the fall detection system further comprising a processing unit configured to determine the orientation of the user device, determine which of the plurality of proximity sensors is facing downwards from the determined orientation; control the determined one or more proximity sensors to measure the proximity of the user device to the ground or floor; and process the measurements from the movement sensor and the measurements from the proximity sensor to determine if the user has fallen.

According to a sixth aspect of the invention, there is provided a method for detecting falls using a fall detection system, the fall detection system comprising a plurality of proximity sensors arranged to face in generally the same direction to form an array, the method comprising measuring the movements of a user using a movement sensor; controlling the array to measure the distance to an object in different directions; processing the distance measurements in different directions to determine the extent or extendedness of the object; determining if the object is the ground or floor from the determined extent or extendedness of the object; and processing the measurements of the movements of the user and the distance measurements in the event that the object is determined to be the ground or floor to determine if the user has fallen.

According to a seventh aspect of the invention, there is provided a fall detection system comprising a user device configured to be worn or carried by a user, the user device comprising: a plurality of proximity sensors for measuring the proximity of the user device to the ground or a floor arranged to face in generally the same direction to form an array; and a movement sensor for measuring the movements of the user; the fall detection system further comprising a processing unit configured to control the array to measure the distance to an object in different directions; process the distance measurements in different directions to determine the extent or extendedness of the object; determine if the object is the ground or floor from the determined extent or extendedness of the object; and process the measurements of the movements of the user and the distance measurements in the event that the object is determined to be the ground or floor to determine if the user has fallen.

BRIEF DESCRIPTION OF THE DRAWINGS

Exemplary embodiments of the invention will now be described, by way of example only, with reference to the following drawings, in which.

DETAILED DESCRIPTION OF THE PREFERRED EMBODIMENTS

As described above in the Background section, it has been found that existing fall detection methods based on the analysis of measurements from movement sensors in a wrist-worn fall detection system do not provide a sufficiently high detection rate while limiting the number of false alarms due to the movements and apparent impacts of the wrist that can occur in normal daily activities, such as walking, sitting, etc., that do not otherwise result from falls by the user. These existing fall detection methods derive features including orientation change, height change, vertical velocity and/or impact magnitude from the movement sensor measurements to determine if the user of the fall detection system has suffered a fall.

Thus, in accordance with the invention, the reliability of a wrist-worn fall detection system is improved by including an additional sensor in the fall detection system that can measure the proximity of the fall detection system to the ground or floor. The proximity sensor may use one or more modalities for detecting the proximity of the fall detection system to the ground or floor.

In preferred embodiments, the proximity sensor uses sound or light to measure the distance to an object by measuring the time between the emission of a pulse of sound or light and the receipt of an echo (reflection) of the pulse. The round-trip distance (and thus the distance to the object that produced the echo) can be determined using the known speed of sound or light in a particular medium and the measured time. Furthermore, the intensity of the reflected sound or light signal may be used as a measure of the distance and/or surface type. In some cases, since the distance between the proximity sensor and the object may be changing as the distance is measured, there may be a Doppler shift in the received reflection of the pulse, and this Doppler shift can be analysed as part of the proximity detection.

The proximity sensor can also or alternatively measure changes in capacitance or inductance to estimate the proximity to an object. Changes in the electric or magnetic field for a capacitive or inductive proximity sensor, respectively, can indicate whether an object is in proximity to the sensor.

As a further alternative or addition, the proximity sensor can comprise a light sensor that measures light brightness, and the brightness level can be used to estimate the proximity to an object. For example, when the measured brightness level is low (possibly following a period where the measured brightness was relatively high), this can indicate that the light sensor has been occluded by an object, such as the floor. A light sensor can also or alternatively determine proximity by measuring focus depth to an object and/or breadth of view.

The proximity of the fall detection system to the floor or ground measured using this sensor will provide another feature that can be used in the fall detection algorithm to determine if the user has fallen.

Typically, a proximity sensor according to the preferred embodiments consists of an emitter which emits a short pulse of sound or light and a receiver which measures the corresponding signal that is reflected off of the surface of an object that is in proximity to the sensor. Proximity sensors are often designed so that the emitter and receiver are placed in close proximity, while preventing a direct coupling between the two. The sensitivity response of the receiver is also designed to closely match the response of the emitter's signal. For example an ultrasound-based proximity sensor that emits an ultrasonic signal at 40 kHz will preferably include a receiver with its peak response centred at 40 kHz. The light transducers found in some computer mice may be suitable for use as a proximity sensor in a fall detection system according to embodiments described herein. In those embodiments, it may also be useful to use that light sensor to measure the displacement of the sensor over the object or surface (e.g. floor).

Figure 1:
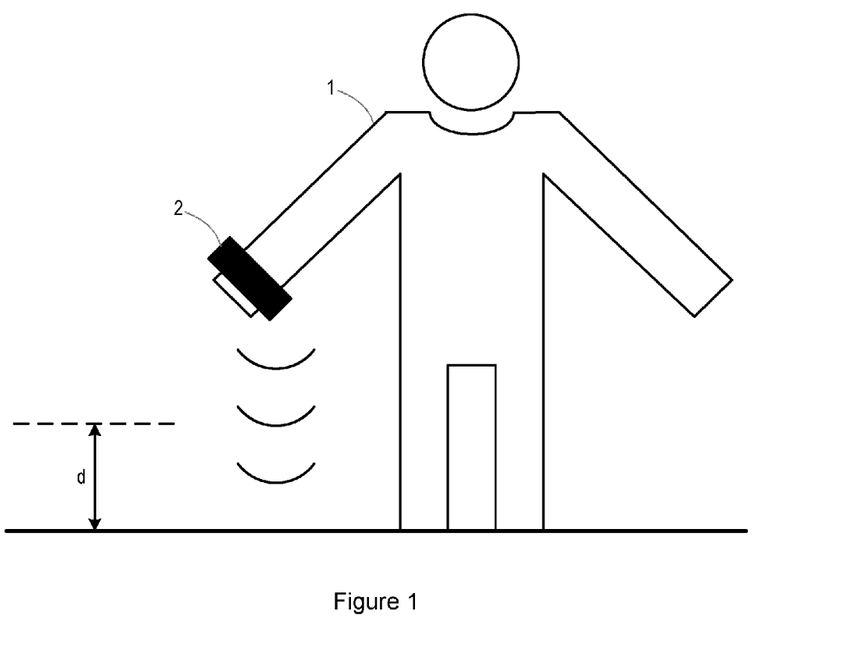
FIG. 1 shows a user wearing a wrist-worn fall detection system according to the invention, with the user upright or walking.
Figure 2:
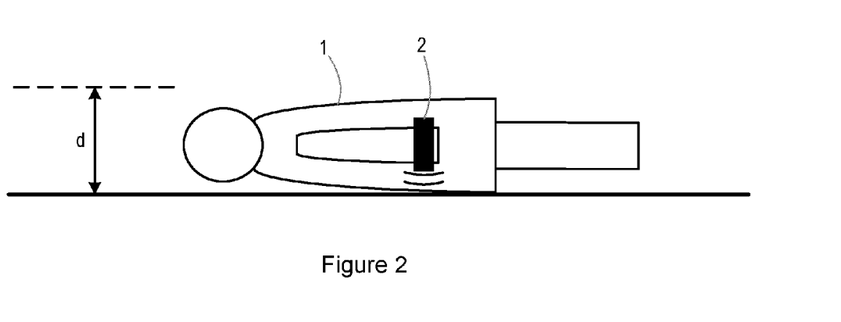
FIG. 2 shows a user wearing a wrist-worn fall detection system according to the invention, with the user lying on the ground or floor.

FIGS. 1 and 2 illustrate the use of a fall detection system that includes a proximity sensor in determining whether a user has fallen. The user 1 is carrying or wearing a fall detection system 2 that includes a proximity sensor on their wrist. The proximity sensor in the fall detection system 2 preferably (but not necessarily) emits pulses of sound or light as described above to measure the distance to the ground or floor. The fall detection system 2 can apply a threshold to the measurements from the proximity sensor to determine if the fall detection system 2 (and thus the wrist of the user 1) is close enough to the ground or floor to suggest a possible fall. This threshold distance is denoted d in FIGS. 1 and 2 and has a typical value in the region of 0.1 meters to 0.5 meters.

When the user 1 is standing or walking normally as in FIG. 1, the distance measured by the proximity sensor in the fall detection system 2 will be greater than the threshold distance, suggesting that the user 1 is not lying on the ground or floor. This feature reduces the likelihood of the fall detection algorithm detecting that a fall has taken place. Using conventional fall detection algorithms, if the user 1 accidently bumps their wrist against some furniture, producing a measurable impact, and there is some orientation and height change (which can occur in the normal movements of the user's wrist), a fall might be detected. However, the measurement of the proximity sensor used according to the invention will indicate that the wrist is not close to the floor or ground, which will reduce the likelihood of this event being classified as a fall. Also, it may be that the configuration of the fall detection algorithm (e.g. certain assumptions, thresholds and/or parameters used in the algorithm) may produce an output indicating a fall (or not), which the use of a proximity sensor according to the invention can help to isolate as false alarms. For example, if the user lifts their wrist and drops it again, the algorithm might happen to examine the height change in the time interval between the lift and drop and conclude that a significant height drop has occurred, but if the algorithm examined the height drop from the height just before the lift, no height drop would be detected.

However, if the user 1 has fallen and they are lying on the ground or floor as shown in FIG. 2, the distance measured by the proximity sensor in the fall detection system 2 will be less than the threshold distance d, and the detection of this feature can increase the likelihood of a fall being detected by the fall detection algorithm.

Figure 3:
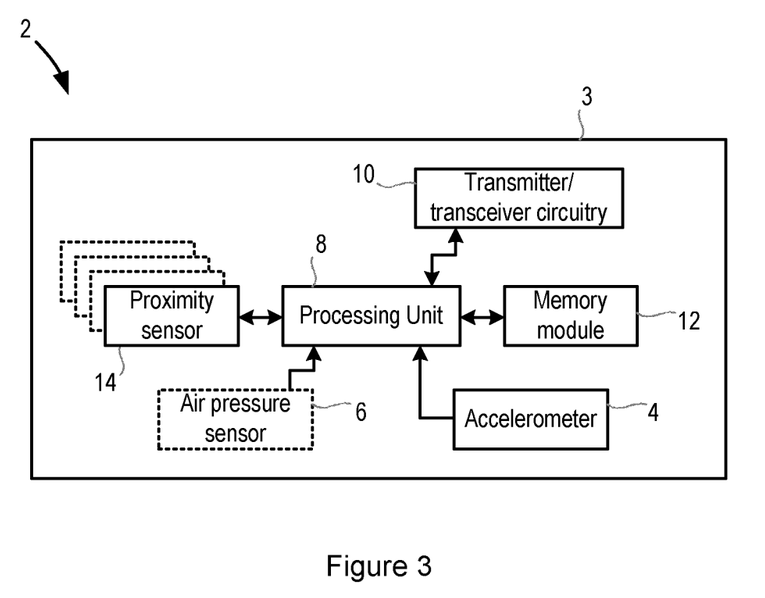
FIG. 3 is a block diagram of a fall detection system in accordance with an embodiment of the invention.

A fall detection system 2 according to an embodiment of the invention is shown in FIG. 3. In a preferred embodiment of the invention, the fall detection system 2 is comprised in a user device 3 that is designed to be worn by a user on their wrist, although it will be appreciated that the invention is not limited to this use, and the user device 3 could instead be designed to be worn at the user's waist, on their chest or back, or as a pendant around their neck. In the wrist-worn embodiment, the user device 3 may be provided in the form of a wrist band, a wrist strap or a watch.

The fall detection system 2 (user device 3) comprises one or more sensors for measuring the movements of the user 1. In this embodiment, the fall detection system 2 comprises two movement sensors, an accelerometer 4 that measures the (three-dimensional) accelerations experienced by the fall detection system 2 and an air pressure sensor 6 that measures air pressure or changes in air pressure. The movement sensors 4, 6 are connected to a processing unit 8. The processing unit 8 receives measurements from the movement sensors 4, 6 and processes the measurements to determine if the user 1 of the fall detection system 2 may have suffered a fall. Although two movement sensors are shown in this embodiment, it will be appreciated that fall detection systems 1 according to alternative embodiments may comprise only one movement sensor (for example just the accelerometer 4). In yet further embodiments, the fall detection system 2 can comprise additional or alternative types of movement sensors, such as a gyroscope or magnetometer. In some embodiments, the fall detection system 2 may also comprise sensors for measuring physiological aspects, such as a skin conductance sensor and/or a photoplethysmograph (PPG) sensor.

The fall detection system 2 also comprises transmitter or transceiver circuitry 10 that allows the fall detection system 2 to transmit an alarm signal in the event that a fall is detected, or help is otherwise requested by the user 1 (for example by pressing a personal help button (PHB) present in the system 2). The transmitter or transceiver circuitry 10 can be configured to communicate with a base station associated with the fall detection system 2 (which can then issue an alarm or summon help from a healthcare provider or the emergency services) or via a public telephone network (such as a mobile telecommunications network) to a remote station (for example located in call centre of a healthcare provider). Where the transmitter or transceiver circuitry 10 is configured to communicate with a base station, the circuitry 10 may be configured according to any known wireless technology, for example Wi-Fi, Bluetooth, Near Field Communication (NFC), etc. Where the transmitter or transceiver circuitry 10 is also or alternatively provided to enable communications with a public telephone network, such as a mobile telephone network, the circuitry 10 may be also or alternatively configured for use with any suitable type of second-, third- or fourth-generation communication network, including GSM, WCDMA, LTE, etc. Also, although not shown in FIG. 3, the fall detection system 2 may comprise a loudspeaker and/or microphone for enabling a user 1 to communicate with the healthcare provider or the emergency services.

The fall detection system 2 also comprises a memory module 12 that is connected to the processing unit 8 and that can store measurement data from the movement sensors 4, 6, the results of processing or pre-processing of the measurement data and/or computer readable code to enable the processing unit 8 to execute the fall detection algorithm and/or otherwise control the operation of the fall detection system 2.

It will be appreciated that the memory module 12 may only store the latest measurement data and that measurement data may also be transmitted using transmitter or transceiver circuitry 10 to a remote server or via a base station for storage.

In accordance with the invention, the fall detection system 2 comprises one or more proximity sensors 14 that measure the distance of the fall detection system to the ground, floor or other object. The proximity sensor(s) 14 are connected to the processing unit 8. The proximity sensor 14 may be mounted in a main housing of the fall detection system 2, or it may be mounted in part of a strap or band that is used to attach the fall detection system 2 to the user 1.

As noted above, the proximity sensor 14 preferably measures distances to objects (e.g. the ground or floor) by emitting pulses of sound or light and measuring the time of flight from the emission of the pulse to the receipt of an echo reflected from the object. The proximity sensor 14 may comprise a sound or light transducer that performs both the transmission and reception functions, while in other embodiments the proximity sensor 14 may comprise separate transmitter/emitter and receiver components.

In particular embodiments, the proximity sensor 14 can measure distances using ultrasound. When employing ultrasound, a short pulse with a frequency beyond that of human hearing (i.e. greater than 20 kHz) is emitted by the ultrasound transmitter. The receiver then listens for the reflected pulse or echo. Given the speed of sound in the specific medium and the delay between the transmitted pulse and the received echo, the round-trip distance can be determined. The distance between the proximity sensor 14 and the point of reflection corresponds to half the round-trip distance. The use of ultrasound to measure the distance is advantageous since ultrasound signals have good directionality (so reflections are likely to only occur from objects generally in 'front' of the transmitter) and there is almost no interference from high-intensity environmental sounds since they will be at a lower frequency than the ultrasound signals.

As the speed of sound in a specific medium depends on the temperature of that medium, in some embodiments the fall detection system 2 includes a temperature sensor and the measured temperature is used to correct the speed of sound value used in the distance (proximity) calculation. Instead of providing a temperature sensor, if correction of the speed of sound is required for temperature, the fall detection system 2 can include a table stored in the memory module 12 that maps the time-of year (e.g. in terms of season, month, etc) and/or time-of-day to a typical temperature (or a speed of sound based on that typical temperature), that is used to calculate the distance (proximity).

In alternative embodiments, the proximity sensor 14 can include a light-based transducer, for example an infrared LED or laser combined with a photodiode which is sensitive to the wavelength of the light emitted by the LED, to measure the distance from the sensor 14 to an object.

The proximity sensor 14 can output the measured distance to the processing unit 8 which translates the measured distance to a proximity measure (e.g. proximate an object or floor or not proximate an object or floor) by comparing the distance to a threshold value, or, alternatively the proximity sensor 14 itself can translate the measured distance into the proximity measure and output the proximity measure to the processing unit 8.

In some embodiments, as described in more detail below with reference to FIG. 5, the fall detection system 2 may comprise multiple proximity sensors 14 that can be distributed around the housing of the fall detection system 2 or wrist band or belt around the waist and arranged in different orientations to enable the distance to the ground, floor or other object to be measured regardless of the orientation of the fall detection system 2 (and thus regardless of the orientation of the user's wrist).

Where multiple proximity sensors 14 are provided, sensors 14 can be placed in pairs (or more) facing generally the same direction and they can be driven together to create beaming effects in the emitted ultrasound signal. This can enable the width of the "viewing" direction of the sensor 14 to be narrowed, and hence provide a more accurate measurement of the distance in the direction of the beam. This can also enable the direction of the beam to be varied by varying the phase of the signal (pulse) by which neighbouring sensors 14 (pairs/triples in the example) are excited, in relation to the wavelength used. As described in more detail below, varying the direction of the beam allows the proximity measurement to be executed in different directions, which in turn provides a measure of the extendedness of the (proximate) object. In this case, where sensors 14 are distributed around the fall detection system 2 to allow distance to be measured regardless of the orientation of the fall detection system 2, the sensors 14 may be mounted in pairs or triples for beam control, with multiple pairs/triples distributed around the fall detection system 2 for global coverage.

Multiple proximity sensors 14 may also consist of proximity sensors of different types grouped into one or more clusters which are distributed around the housing of the fall detection system 2. Such an embodiment is beneficial to overcome certain limitations of a given proximity sensor. For example, on the one hand, dark-coloured surfaces absorb light, and thus an ultrasound proximity sensor would provide more accurate proximity detection. On the other hand, sound-absorbing materials may lead to poor ultrasound proximity detection, while infrared-based proximity detectors may be unaffected.

Multiple proximity sensors 14 may also or alternatively be provided that are to be placed at multiple sites on the user's body. This allows the proximity of different parts of the user's body to the ground or floor to be measured, increasing the reliability of the proximity detection (for example in case the proximity sensor 14 on one part of the body gives a false positive measurement indicating that the body part is not close to the ground or floor). In this case, at least one of those proximity sensors 14 can be integrated into a separate housing or wearable component to the rest of the components of the fall detection system 2 shown in FIG. 1. In that case, those other proximity sensors 14 will be provided with means to enable the proximity or distance measurements to be communicated to the processing unit 8 for analysis. The measurements may be communicated through a wired or wireless (e.g. WiFi, Bluetooth, Near Field Communication (NFC) or ZigBee) connection to the main fall detection system unit 2.

Those skilled in the art will appreciate that FIG. 3 only shows the components of the fall detection system 2 required to illustrate the invention, and the fall detection system 2 can comprise other components to those shown. For example, the fall detection system 2 will comprise a battery or other portable power source. The fall detection system 2 may further comprise an audible alarm unit that can be activated by the processing unit 8 in the event that the processing unit 8 determines that the user 1 has suffered a fall. The fall detection system 2 may also be provided with a button (also not shown in FIG. 3) that allows the user 1 to manually activate the audible alarm unit if they require assistance (or, in some cases, to deactivate the alarm if assistance is not required). In further or alternative embodiments, the fall detection system 2 may comprise a satellite positioning system (SPS) receiver, such as a Global Positioning System (GPS) receiver, for tracking the location of the fall detection system 2. Information on the location of the fall detection system 2 can be transmitted to the call centre in the event that an alarm is triggered to enable help or assistance to be sent to the right location.

In alternative embodiments to that shown in FIG. 3, the fall detection system 2 can comprise a user device 3 that generally corresponds to the user device 3 shown in FIG. 3, but the fall detection system 2 further comprises a base unit that is to be located in the home of the user 1 and that communicates wirelessly with the user device 3. The base unit may also act as a charging station for the user device 3. The base unit may comprise circuitry for enabling communications between the user and a remote call centre (such as the emergency services) via a public switched telephone network and/or a mobile communications network, and/or may provide a connection to the Internet. In some implementations of this system 2, the processing and operations according to the invention can be performed by the processing unit 10 in the user device 3, with the base unit being provided merely to facilitate communications with the remote call centre/emergency services/Internet. In alternative implementations, the user device 3 can communicate the measurements obtained by the movement sensors 4, 6 and proximity sensor(s) 14 to the base unit using the transmitter/transceiver circuitry 10, and a processing unit in the base unit can perform the processing and operations according to the invention using the measurements. This latter embodiment has the advantage that the power consumption of the user device 3 can be substantially reduced. Where the user device 3 connects to a base unit owned by the user 1, the connection can be made using any known wireless technology, for example Wi-Fi, Bluetooth, Zigbee, Near Field Communication (NFC), etc.

As discussed below, the fall detection system 2 uses a fall detection algorithm that processes the proximity value measured by the proximity sensor 14 together with other features (e.g., height change, impact, orientation, etc.) derived from the measurements from the movement sensor(s) 4, 6 to determine if the user 1 has fallen. In some embodiments, when full fall detection processing is carried out, it is determined whether the set of feature values (including the proximity sensor value) is in a (multidimensional) region corresponding to a fall. Preferably, a value indicating the likelihood of a fall is determined for the set of feature values, and this likelihood is compared to a threshold to determine if a fall has occurred. Alternatively, each individual feature value can be compared to a respective threshold, and a fall detected if a certain number of features exceed their threshold value. In another alternative, the full fall detection algorithm can be executed in stages, with a feature or various features being derived at each stage, and each stage is only triggered if the features derived in the previous stage are consistent with a fall having taken place. The derived features are then tested in a classifier to determine if a fall has taken place. This type of staged computation of feature values, with each value being tested against a threshold, is referred to as a state machine.

Figure 4:
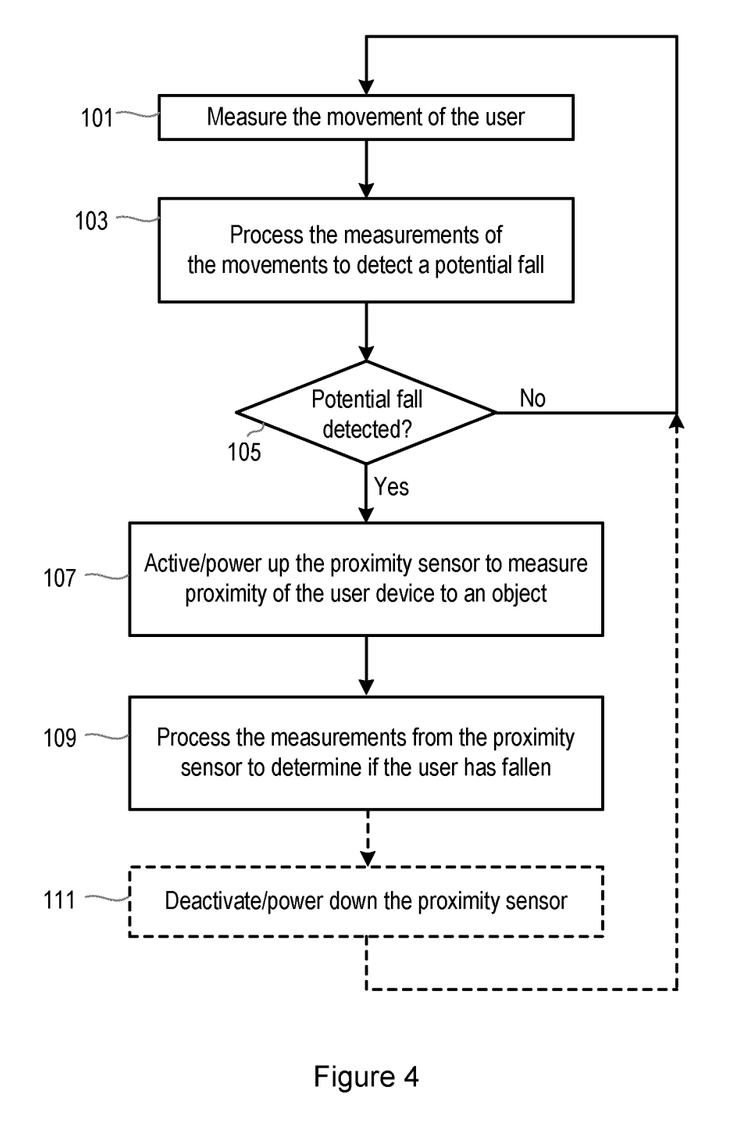
FIG. 4 is a flow chart illustrating a method of operating a fall detection system according to a first embodiment.

A method of operating the fall detection system 2 to detect whether the user 1 has fallen is shown in FIG. 4. In this embodiment, it is recognised that a proximity sensor 14 can consume a lot of power if it is active all of the time, and as the proximity sensor 14 may only provide a useful measurement of its feature (i.e. the proximity of the fall detection system 2/user 1 to the ground or floor after an impact or height change event) once a fall has occurred, the proximity sensor 14 is only activated if a potential fall is detected following some processing of the measurements from one or more of the movement sensors 4, 6. This embodiment enables a proximity sensor 14 to be used to improve the reliability of the fall detection algorithm without substantially increasing the average power consumption of the fall detection system 2.

Thus, in a first step, step 101, the movements of the user 1 are measured using the one or more movement sensors 4, 6. That is, one or more of the movement sensors 4, 6 are active (i.e. powered) and measurements of the movements are provided by the sensors 4, 6 to the processing unit 8 for analysis. In this step, the proximity sensor(s) 14 are inactive and thus not emitting sound or light (as appropriate for the type of sensor). In some cases the processing unit 8 can control the fall detection system 2 so that power is not supplied to the proximity sensor(s) 14, but in other cases power can continue to be supplied to the proximity sensor components, but the processing unit 8 controls the proximity sensor(s) 14 so that they do not activate their transducers.

In step 103, the processing unit 8 (or, in the alternative embodiment described above, the processing unit in a base station) processes the measurements of the movements of the user 1 obtained in step 101 to determine whether the user 1 may have suffered a fall. At this stage, the measurements are only processed to determine whether a fall may have potentially occurred (i.e. the measurements are processed to see if there is some indicator or trigger feature that a fall has taken place), and therefore whether further measurements and/or more detailed analysis of the measurements (i.e. execution of the full fall detection algorithm) may be required to confirm whether a fall has actually occurred and an alarm needs to be triggered. As a result, it is not necessary for the processing unit 8 to execute a full fall detection algorithm at this stage.

A fall can be broadly characterised by, for example, a change in altitude of around 0.5 to 1.5 meters (the range may be different depending on the part of the body that the fall detection system 2 is to be worn and the height of the user 1), culminating in a significant impact, followed by a period in which the user 1 does not move very much. Thus, in a fall detection algorithm as described above, movement sensor measurements can be processed to extract values for one or more features including a change (specifically a reduction) in height/altitude (which is usually derived from the measurements from the air pressure sensor 6, but can also or alternatively be derived from the measurements from the accelerometer 4, for example if the air pressure sensor 6 is omitted), a maximum activity level (i.e. an impact) around the time that the change in altitude occurs (typically derived from the measurements from the accelerometer 4), a period in which the user 1 is relatively inactive following the impact (again typically derived from the measurements from the accelerometer 4), the vertical velocity, the occurrence of free fall (typically derived from measurements from the accelerometer 4), a change in orientation upon falling (typically derived from the measurements from the accelerometer 4 or from a gyroscope, if present) and an indication of a height/altitude increase after a detected impact.

In step 103 the processing unit 8 preferably processes the movement measurements to detect a selected trigger feature that typically occurs during a fall, with the detection of this selected (trigger) feature providing an indication that a fall has potentially occurred (the other features of a fall, for example those listed above, are not computed by the processing unit 8 at this stage). As the fall detection system 2 needs to continuously monitor the user 1 for a fall, this limited processing of the movement sensor measurements for a single trigger feature helps to minimise the power consumption of the fall detection system 2.

In a preferred embodiment of step 103 (which is particularly preferred when the fall detection system 2 comprises an air pressure sensor 6), the processing unit 8 processes the movement measurements to detect if a certain height change (and in particular a height drop) has occurred. The required height change can be 0.5 meters, or any other suitable value taking into account where on the user's body the fall detection system 2 is carried and/or on the height or other physical characteristics of the user 1. In an alternative preferred embodiment (which is particularly preferred when the fall detection system 2 comprises an accelerometer 4 but not an air pressure sensor 6), the processing unit 8 can process the movement measurements to detect if an impact (which a magnitude greater than a threshold value) is present in the movement measurements to identify if a fall has potentially occurred. In an alternative preferred embodiment, the processing unit 8 can process the movement measurements to detect if a different feature or further features, e.g. a free-fall longer than a threshold time period, are present in the movement measurements to identify if a fall has potentially occurred. In some embodiments, it is not necessary for the processing performed on the movement measurements in step 103 to produce a particularly refined (i.e. accurate) value for the selected feature, which can enable a value for the feature to be determined with reduced processing effort.

It will be appreciated that the processing performed in step 103 can be performed in real-time or near real-time to detect a potential fall as soon as it has occurred, or even to detect a potential fall during the physical act of falling itself. For example, with real-time or near real-time processing of the accelerometer 4 and/or air pressure sensor 6 measurements to detect a height change and/or free fall, a potential fall (as indicated by a height drop greater than a threshold height drop or free fall for longer than a threshold time period) can be detected before the user 1 impacts the ground.

In step 105 it is determined whether a potential fall has been detected. For example, where step 103 comprises determining the height change, a potential fall is detected if a drop in height of at least 0.5 meters is detected in the movement measurements. Where step 103 comprises determining an impact magnitude, a potential fall is detected if an impact is detected that has a magnitude greater than a threshold value.

If no potential falls are detected in step 103 (e.g. there is no or an insufficient height drop or an impact of insufficient magnitude), the method returns to step 101 and further measurements of the movements of the user 1 are collected and analysed for a potential fall.

However, if a potential fall is detected in step 103 (e.g. a height drop of at least 0.5 meters is detected or an impact with a sufficient magnitude), then the method moves to step 107 in which the proximity sensor(s) 14 is activated in order to measure the proximity of the part of the body of the user 1 to which the fall detection system 2/user device 3 is attached to the ground or floor. Step 107 may comprise the processing unit 8 controlling the fall detection system 2 so that power is supplied to the proximity sensor(s) 14, thereby activating the transducers to emit light or sound as appropriate, or may comprise the processing unit 8 directly controlling the proximity sensor(s) 14 to activate their transducers. The distance(s) measured by the proximity sensor(s) 14 or the proximity measure(s) (if determined by the proximity sensor(s) 14) are output to the processing unit 8.

As noted above, with real-time or near real-time processing of the movement sensor measurements in step 103, a potential fall may be detected while the actual fall is still in progress, which can result in the proximity sensor(s) 14 being activated/powered on before an impact occurs.

In some embodiments, particularly where the fall detection algorithm is based on a state machine concept, it is possible for the detection of a potential fall in step 105 to be based on the staged detection of multiple fall features before it is decided to activate the proximity sensor 14 in step 107.

In some embodiments (not shown in FIG. 4), following the detection of a potential fall in step 105, an alarm can be issued by the fall detection system 2 in order to start the process of getting help to the user 1.

In step 109 the processing unit 8 (or processing unit in a base station in the alternative embodiment) processes the measurements from the proximity sensor(s) 14 to determine if the user 1 has fallen.

In some embodiments, following the detection of the potential fall in step 105, step 109 can comprise simply determining whether the fall detection system 2 is proximate the ground or floor and accepting or rejecting the potential fall on that basis (i.e. if the system 2 is proximate the ground or floor (e.g. the distance<d) the potential fall is confirmed, and if the system 2 is not proximate the ground or floor (e.g. the distance>d) the potential fall is rejected).

In other embodiments, following the detection of the potential fall in step 105, step 109 can comprise inputting the measured proximity and the previously computed trigger features into a classifier to determine whether a fall has occurred. In yet further embodiments, step 109 can comprise the continuation of a state machine process in which one or more further features are computed from the movement sensor measurements, and then a fall detected after the features are input to a classifier. In yet another embodiment, when the fall detection algorithm is not based on a state machine concept, step 109 can comprise determining one or more further fall features from the movement sensor measurements and processing those fall features along with the proximity measurement to determine if the user 1 has fallen.

In some embodiments, particularly where a height change is computed from the movement sensor measurements, a change in proximity of the fall detection system 2 to the ground or floor can be calculated (if the proximity sensor 14 is activated early enough during the ongoing fall) and compared to the computed height change, and the result of this comparison can be input to the fall detection algorithm.

The analysis performed by the processing unit 8 in the embodiments of step 109 will not be described in detail herein since those skilled in the art will be aware of various algorithms and techniques that can be used to determine whether a user has suffered a fall from movement sensor measurements. As noted above, in some algorithms a set of feature values derived from the measurements is provided to a classifier that has been optimised to decide between falls and non-falls based on the feature values. The proximity measurements can be input into this classifier as an additional feature value and used to affect or derive a likelihood value that a fall has occurred. As discussed below with reference to FIGS. 7 and 8, another or an alternative feature that can be input to the threshold sequence (state machine) or classifier that is derived using the proximity sensor 14 is the extent or 'extendedness' of the object to which the distance has been measured. This extent or extendedness indicates how likely the object to which the distance has been measured is a floor or the ground.

After completing the processing of the measurements in step 109 (or in some cases after measuring the distance to an object in step 107 and prior to step 109), the proximity sensor(s) 14 are deactivated/powered down to minimise the power consumption of the fall detection system 2 (step 111).

Alternatively, rather than deactivate or power down the proximity sensor(s) 14 after the processing of the measurements has occurred in step 109, the proximity sensor(s) 14 can be used to detect whether the user 1 gets up after a detected fall. Thus, if a fall is detected in step 109, the proximity sensor(s) 14 can remain powered or activated to continue measuring the distance between the sensor(s) 14 and an object/floor. The processing unit 8 can monitor the measured distances output by the proximity sensor(s) 14 to determine if the user 1 gets up (for example by detecting if the measured distance becomes greater than the threshold distance d). Once it has been detected that the user 1 has got up, the proximity sensor(s) 14 may be powered down/deactivated as shown in step 111. In some cases, the detection of whether the user 1 has got up using the proximity measurements can also take into account the orientation of the fall detection unit 2 (as discussed below) in order to distinguish a user 1 getting up from the floor from the user 1 reaching upwards to try and get up.

Although not shown in FIG. 4, on detection or confirmation of a fall in step 109, the fall detection system 2 can trigger an alarm to summon help to the user 1. Triggering an alarm may comprise activating an audible alarm unit in the fall detection system 2, and/or initiating a call or otherwise sending an alarm message or signal to a remote location (such as a call centre or the emergency services).

As noted above, in some embodiments the fall detection system 2 can comprise multiple proximity sensors 14 that can be distributed around the housing of the fall detection system 2 or wrist band and arranged in different orientations to enable the distance to the ground, floor or other object to be measured regardless of the orientation of the fall detection system 2 (and thus regardless of the orientation of the user's wrist). A fall detection system 2 according to this embodiment is shown in FIG. 5. In this embodiment the fall detection system 2/user device 3 is in the form of a wrist band with five proximity sensors 14a-14e distributed around the wrist band (although more or less proximity sensors can be provided). The proximity sensors 14a-14e each face outwards from the wrist band (as indicated by the dashed arrows). The wrist band also includes a housing 16 that contains the other components of the fall detection system 2 (e.g. as shown in FIG. 3).

Figure 5:
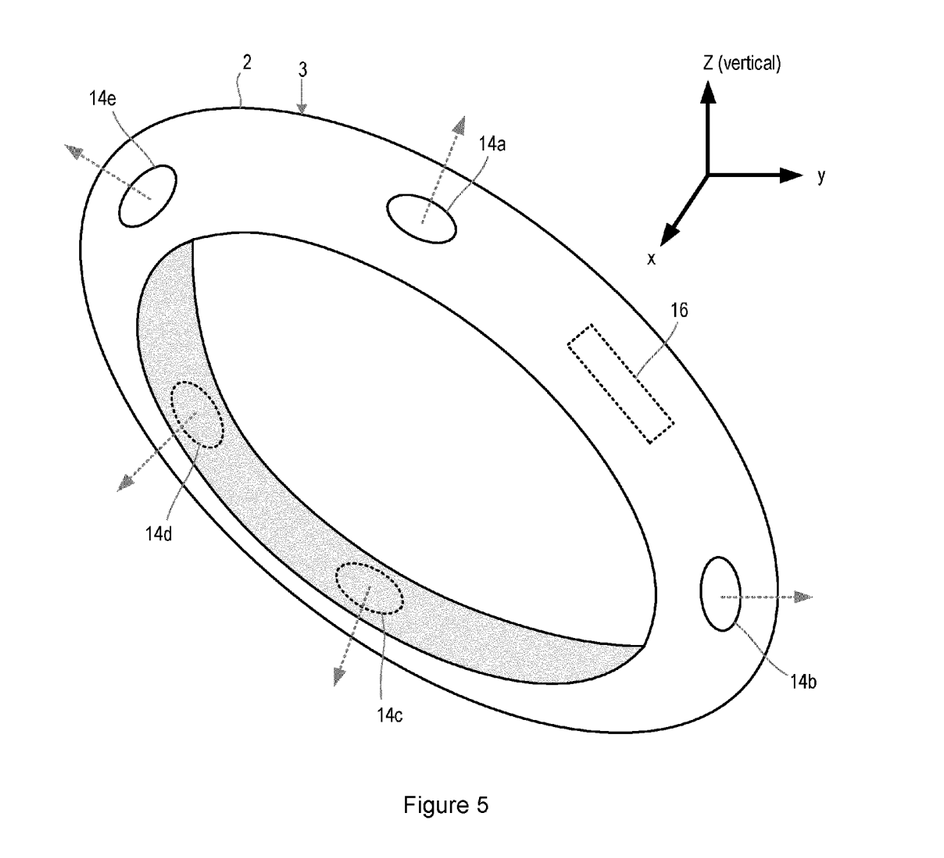
FIG. 5 is an illustration of a fall detection system according to a second embodiment.

When used with the fall detection system 2 in FIG. 5, step 107 of FIG. 4 can comprise activating or powering up all of the proximity sensors 14a-14e if a potential fall is detected. In some embodiments, the proximity sensors 14a-14e can be activated in a round-robin (i.e., consecutive) approach to prevent cross-talk between the proximity sensors, and a proximity map as a function of the azimuth angle can be calculated with respect to the location of one of the proximity sensors 14a-14e as a reference. This 'reference' sensor can be the proximity sensor 14 that is facing downward.

Figure 6:
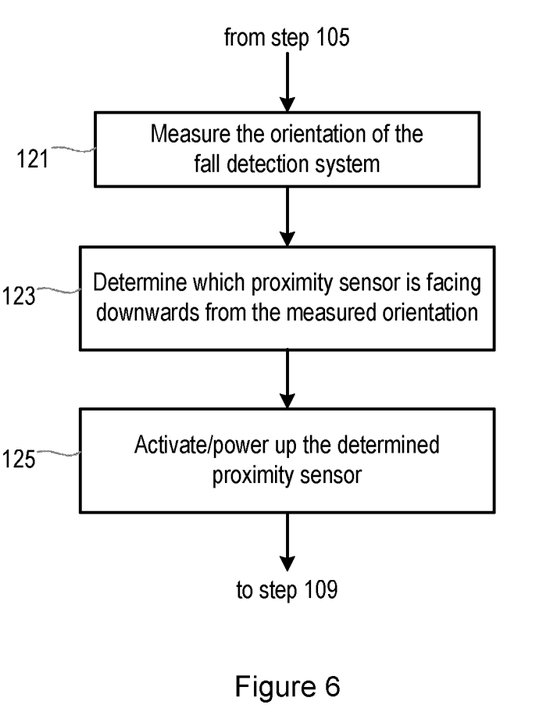
FIG. 6 is a flow chart illustrating a method of operating a fall detection system according to the second embodiment.

However, in preferred implementations, only the proximity sensor 14 that is facing downwards (or the nearest to facing downwards) is activated or powered up if a potential fall is detected. In this way the distance to the ground or floor can be measured regardless of the orientation of the wrist and also regardless of the orientation in which the fall detection system 2 is attached to the user's wrist, without having to activate or power up all of the proximity sensors 14. FIG. 6 shows various exemplary steps for implementing this feature in the fall detection system 2 in place of step 107 in FIG. 4.

In step 121, which takes place after a potential fall is detected in step 105, the measurements from the accelerometer 4 in the fall detection device 2 are processed to identify the component of acceleration due to gravity and the direction in which gravity is acting. The direction in which gravity is acting indicates the orientation of the fall detection device 2, and more precisely it indicates the vertical direction and hence the direction at which the (proximate) floor, if present, should be expected.

In step 123, it is determined which of the proximity sensors 14a-14e is facing downwards from the determined orientation of the fall detection system 2. To achieve this, the fall detection device 2 can be preconfigured with the identity of the proximity sensor 14a-e to use for a given orientation of the fall detection system 2 (although those skilled in the art will appreciate that this can be implemented in alternative ways). Thus, this step can comprise looking up the appropriate proximity sensor 14a-e to use for the determined orientation. Given the orientation of the fall detection system 2 shown in FIG. 5, it will be noted that in this case the appropriate proximity sensor to measure the distance to the ground or floor is sensor 14c.

Then, in step 125, the selected proximity sensor 14a-e is activated or powered up to measure the distance to the ground or floor. The method then moves to step 109 of FIG. 4 and proceeds as described above.

When there are two or more proximity sensors 14 arranged in an array around the fall detection system 2, there is an alternative embodiment of the method in FIG. 6 in which step 125 can comprise activating an array of proximity sensors 14 determined in step 123 to be facing downwards (or the nearest to facing downwards) and driving the array of proximity sensors to direct the beam downwards to measure the distance/proximity to the ground or floor.

It will also be appreciated that the method of activating an appropriate proximity sensor 14 (or controlling an array to direct a beam) according to the orientation of the fall detection system 2 can be applied to fall detection systems 2 that do not apply the power reduction method in FIG. 4 and that continuously operate at least one proximity sensor 14 to measure the distance to the ground or floor. In this application of the method, the orientation of the fall detection device 2 is continuously monitored and the proximity sensor 14 that is facing downwards is activated or powered on. If or when the orientation changes so that the active proximity sensor 14 is no longer the most downward facing sensor 14, the fall detection system 2 switches to using the most downwards facing proximity sensor 14.

As a further modification to the embodiment in which there are multiple proximity sensors 14 distributed around a flexible wrist band (or other flexible means for attaching the system 2 to a different part of the body of the user 1, such as a flexible waist belt or neck cord), it is appreciated that since different users have different sized wrists, the flexible nature of the wrist band means that the direction in which each proximity sensor 14 faces will depend on the size and shape of the user's wrist. This variation in orientation for each proximity sensor 14 can be detected by including a respective orientation sensor (such as an accelerometer or magnetometer) with each proximity sensor 14 and determining the direction in which gravity acts at each proximity sensor 14 from the measurements of the acceleration or magnetic field at each site. The determined direction of gravity can then be used to determine the direction in which each proximity sensor 14 is facing, and this information can be used in the method of FIG. 6 to select an appropriate proximity sensor 14 to activate or power up. In some cases, the analysis of the orientation of each proximity sensor 14 may only need to be performed when the system 2 is first switched on by the user 1, although in other cases the analysis can be repeated after some time interval.

As noted above, multiple proximity sensors 14 can be placed in a linear or non-linear 1-, 2- or 3-dimensional array of two, three or more sensors that face generally the same direction and that are driven together to utilise beam forming effects to enable the width of the viewing direction to be changed and/or to enable the direction of the beam to be varied or steered. Varying the direction of the beam allows the proximity measurement to be executed in different directions, which in turn allows a measure of the extent or extendedness of the (proximate) object to be determined.

The extension of the object to which the distance has been measured by the proximity sensor 14 can indicate whether the object is the ground or floor, or some other object, such as a table or door. A large extension (i.e. the object extends for some distance) raises the likelihood that the object is the ground or floor.

Figure 7:
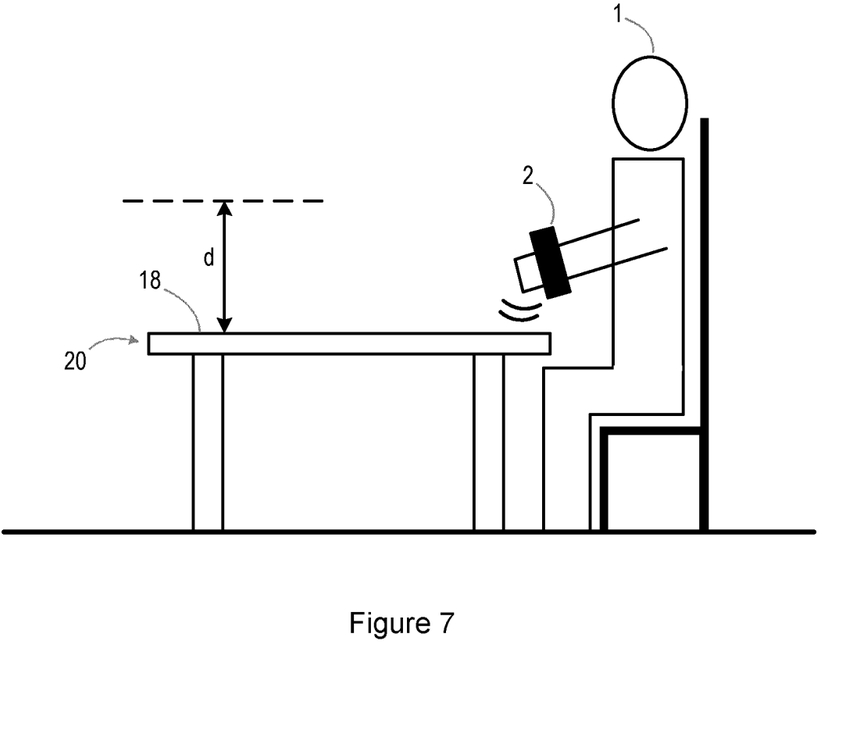
FIG. 7 shows a user wearing a wrist-worn fall detection that is upright and close to a table.

FIG. 7 illustrates a scenario in which determining the extent of a detected object may be useful. In FIG. 7, a user 1 that is wearing a fall detection system 2 on their wrist is sat at a table 18. A proximity sensor 14 in the system 2 will measure the distance to an object below the system 2. As the user's wrist is above the table 18, the distance measured will be quite short, and, in this case, below the threshold distance d that is used to determine if the user 1/system 2 is proximate the ground or floor. Thus, in this scenario the proximity sensor 14 may provide a measurement that incorrectly indicates that the user 1/system 2 is on the floor. However, in certain embodiments, an array of proximity sensors 14 can be controlled to measure the extent of the detected object, which in the example of FIG. 7 will reveal a significantly larger distance to an object when the beam is directed past the edge 20 of the table 18 (particularly in the direction of the elbow of the user 1, which may be known if the orientation of the fall detection system 2 on the user's wrist is known), thereby reducing the likelihood that the measured distance (that is below d) is a distance to the ground or floor.

Figure 8:
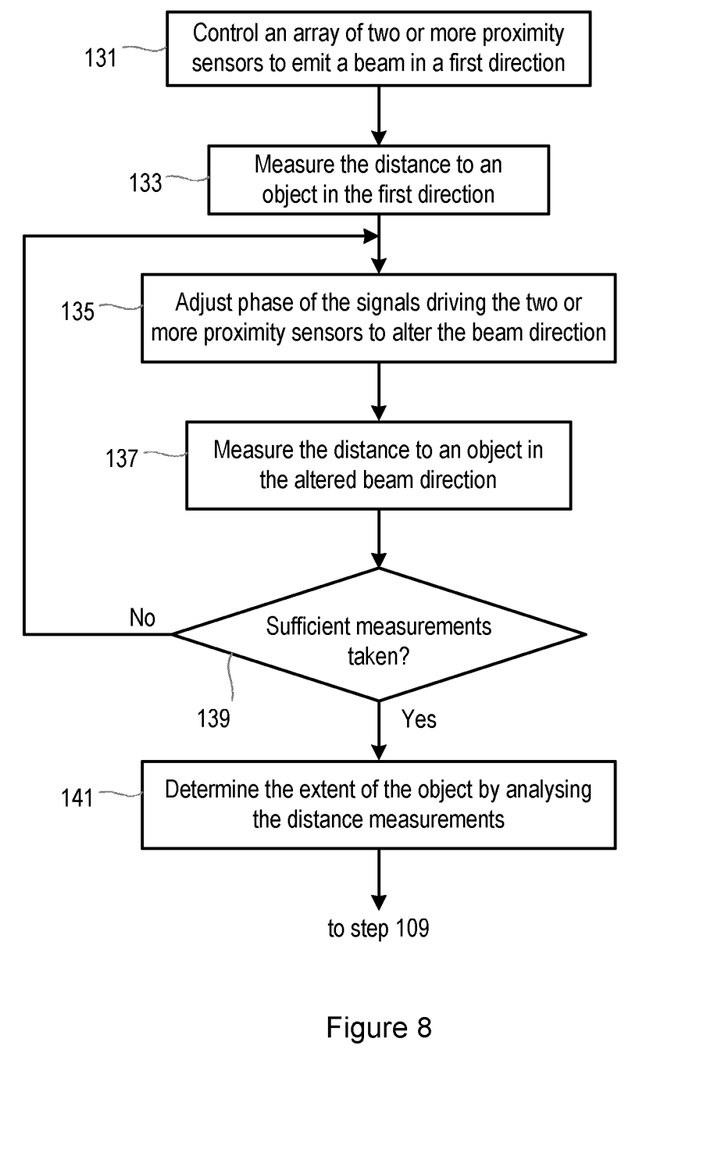
FIG. 8 is a flow chart illustrating a method of operating a fall detection system according to a third embodiment.

FIG. 8 illustrates a method of determining the extent or extendedness of an object that can be performed as part of step 107 of FIG. 4. Once the array of two or more proximity sensors 14 have been activated or powered on following the detection of a potential fall, the processing unit 8 (or a separate processing/control unit associated with the array of proximity sensors 14) controls the array to emit a beam of light or sound (as appropriate) in a first direction (step 131). The control of the array in step 131 comprises applying driving signals to each of the proximity sensors 14 with a known phase difference between the driving signals. The phase difference between the emissions from each sensor 14 will cause the emissions to interfere and produce a directed beam.

The distance to an object is measured using the beam emitted in the first direction (step 133). This step is performed in a similar way to a single proximity sensor 14 embodiment and involves determining the round trip time of the emitted signal and the reflection from the object.

Then, in step 135, the relative phase of the driving signals is changed to alter the beam direction. The distance to an object is measured in the altered beam direction (step 137). Alternatively, where there are multiple arrays of sensors 14 facing in different directions around the housing of the fall detection system 2, at certain direction angles of the beam from a particular array of sensors 14, rather than alter the direction of the beam further, it may be preferable to switch to using another (neighbouring) array of sensors 14 which may be better placed to measure the distance to the object, or to use both arrays for better accuracy.

A number of measurements of the distance to an object in a variety of directions is required in order to take a decision on the extent or extendedness of an object. Thus, in step 139, it is determined whether enough distance measurements have been taken. If not, the method returns to step 135 and repeats for a new direction. Since the aim of this method is to detect whether the user is lying down on the ground or floor, the search for an (abrupt) edge is best performed in the direction of the user's body, i.e. in the direction of the arm, which may be known if the orientation of the fall detection system 2 on the user's wrist is known. Furthermore, the abrupt edge should be within a body's length of the fall detection system 2.

If a sufficient number of measurements have been taken, the method moves to step 141 in which the extent or extendedness of the object is determined by analysing the distance measurements for the different directions. In general, objects of a certain extent, such as a table 18, but with a clear, abrupt edge (e.g. edge 20), will be detectable in the measurements since there will be a significant increase in the measured distance after a series of generally consistent distance measurements. For a flat surface, the distance will equal $(h_0)/\cos(\alpha)$, where $\alpha$ is the angle between the direction of measuring and the vertical (which will be known from the direction of gravity in the measurements from the accelerometer 4), and $h_0$ is the distance in the vertical direction. If the distance to the object is being measured to assist in determining whether a fall has taken place, identifying that the object has a short extent (as in the case of the table 18), can indicate that the likelihood of a fall having taken place is low, since any detected impact may have resulted from the user 1 hitting their hand against the table 18. Of course, it will be appreciated that the ground or floor is not of infinite length and there may be walls nearby, but, in general, at the walls the measured distance will not sharply increase. This can be discerned from the measured distances. The ground or a floor can be characterised by a high proximity (i.e. low distance), a large extension, and no abrupt distance increments at its edges (on all sides).

The determined distance and extent is then processed in step 109 of FIG. 4 with the other feature values derived from the movement sensor measurements.

It will be appreciated that in addition to the round trip time measurements used to determine the extendedness of a detected object, the change in the received echo strength as a function of the relative phase of the beam angle can also be used as a measure of extendedness.

It will also be appreciated that this method of determining the extent or extendedness of the object to which the distance has been measured by the proximity sensors 14 can be applied to fall detection systems 2 that do not apply the power reduction method in FIG. 4 and that continuously operate the array of proximity sensors 14 in order to measure the distance to the ground or floor. In this application of the method, the distance to an object is continuously measured and its extent determined.

In embodiments where multiple proximity sensors 14 are placed at multiple sites on the user's body, it will be appreciated that this method can also be used to calculate the extendedness of the object over these sites.

In the embodiment of FIG. 8, multiple proximity sensors 14 are driven together to create beams and in that way refine the accuracy of the measurement. However, instead of using a beam forming approach and scanning the object for its extendedness, another option is to combine the information from multiple sensors 14 distributed around the fall detection system 2, as in FIG. 5. The more sensors 14 detect the object as being close-by (i.e. within the threshold distance d), the more likely the object is extended, and hence the more likely that the object is the floor, implying the user 1 is lying on the ground.

In addition to the extent or extendedness, another feature value that can be provided by the proximity sensors 14 and that can affect the fall detection process is the relative strength of the echo or reflection of the energy emitted by the proximity sensor 14. The relative strength of the echo or reflection can indicate how hard or soft the surface that reflected the beam is (with a high strength indicating a hard surface and a low strength indicating a soft surface), and can also indicate the reliability of the distance estimate obtained from that surface (with a reliable range estimate requiring a strong echo).

In embodiments where multiple proximity sensors 14 are placed at multiple sites on the user's body, it will be appreciated that this method can also be used to calculate the homogeneity of the surface over these sites.

In another embodiment, the proximity sensors 14 sequentially emit and listen for the echo pulse. Given the position of the proximity sensors 14 with respect to each other a proximity image of the nearby object and environment can be derived from the resulting proximity measurements.

In another embodiment, one or more arrays of proximity sensors 14 can be used to measure the distance to different parts of the body of the user 1 (e.g. by directing the beam in different directions), and then the posture of the user 1 can be inferred from the proximity measurements and a known orientation of the fall detection system 2 (and thus wrist). For example, proximity measurements of different parts of the body from head to feet may enable the fall detection system 2 to distinguish between a sitting posture (e.g. as shown in FIG. 7), a standing posture (e.g. as shown in FIG. 1) and a lying posture (e.g. as shown in FIG. 2).

There is therefore provided a method for detecting falls and a fall detection system that provides increased fall detection reliability compared to conventional techniques.

While the invention has been illustrated and described in detail in the drawings and foregoing description, such illustration and description are to be considered illustrative or exemplary and not restrictive; the invention is not limited to the disclosed embodiments.

Variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A fall detection system comprising:
a user device configured to be worn or carried by a user, the user device comprising:
a plurality of proximity sensors for measuring a proximity of the user device to a ground or a floor; and
a movement sensor for measuring movements of the user; and
a processing unit configured to:
process the measurements from the movement sensor to detect whether the user may have suffered a fall;
activate the plurality of proximity sensors if it is detected that the user may have suffered a fall;
operate the plurality of proximity sensors to enable a direction of a beam formed by the plurality of proximity sensors to be varied or steered, and
process the measurements from the proximity sensors to determine if the user has fallen.

2. The fall detection system as claimed in claim 1, wherein the processing unit is configured to process the movement sensor to detect whether the user may have suffered a fall by processing the movement sensor measurements to determine a change in a height and/or a magnitude of an impact, and it is detected that the user may have suffered a fall if the change in the height is greater than a first threshold value and/or the magnitude of the impact is greater than a second threshold value.

3. The fall detection system as claimed in claim 1, wherein the processing unit is configured to process the measurements from the plurality of proximity sensors and the measurements from the movement sensor to determine if the user has fallen.

4. The fall detection system as claimed in claim 1, wherein the plurality of proximity sensors are distributed in different orientations around the user device.

5. The fall detection system as claimed in claim 4, wherein the processing unit is configured to activate each of the plurality of proximity sensors if it is detected that the user may have suffered a fall.

6. The fall detection system as claimed in claim 4, wherein the processing unit is configured to, on detection that the user may have suffered a fall, process the measurements from the movement sensor to determine the orientation of the user device, determine which of the plurality of proximity sensors is facing downwards from the determined orientation, and activate the proximity sensor that is determined to be facing downwards.

7. The fall detection system as claimed in claim 4, wherein each proximity sensor has an associated orientation sensor for determining an orientation of the proximity sensor, and wherein the processing unit is configured to measure the orientation of each proximity sensor using the orientation sensors, and to determine a direction in which each proximity sensor is facing from the measured orientations.

8. The fall detection system as claimed in claim 1, wherein the plurality of proximity sensors face a same direction to form an array, and wherein the processing unit is configured to operate the array of proximity sensors together to enable a width of a viewing direction of the array to be changed.

9. The fall detection system as claimed in claim 8, wherein the processing unit is configured to operate the array to steer a direction of a beam formed by the array.

10. The fall detection system as claimed in claim 8 wherein the processing unit is configured to control the array to measure a distance to an object in different directions, and to process the distance measurements in different directions to determine an extent or extendedness of the object.

11. The fall detection system as claimed in claim 8, wherein the processing unit is configured to control the array to measure a distance to an object in different directions, and to determine an extent or extendedness of the object from a strength of a received echo as a function of a relative phase of the beam.

12. The fall detection system as claimed in claim 10, wherein the processing unit is configured to determine whether the distance measured by the array of proximity sensors is a distance to the ground, the floor or another object from the determined extent or extendedness of the object.

13. The fall detection system as claimed in claim 12, wherein the processing unit is configured to use a result of the processing to determine whether the distance measured by the object is to the ground, the floor or another object in the processing of the measurements from the proximity sensor and the measurements from the movement sensor to determine if the user has fallen.

14. A method for detecting falls, the method comprising:
measuring movements of a user using a movement sensor;
processing the measurements from the movement sensor to detect whether the user may have suffered a fall;
if it is detected that the user may have suffered a fall, activating a plurality of proximity sensors that measures a proximity of a user device to a ground or a floor;
operating the plurality of proximity sensors to enable a width of a viewing direction of the array to be changed; and
processing the measurements from the proximity sensor to determine if the user has fallen.

15. A non-transitory computer readable medium encoded computer executable instructions, which, when executed by a processor, causes the processor to:
measure movements of a user using a movement sensor;
process the measurements from the movement sensor to detect whether the user may have suffered a fall;
if it is detected that the user may have suffered a fall, activate a plurality of proximity sensors that measures a proximity of a user device to a ground or a floor;
operate the plurality of proximity sensor to determine if the user has plurality of proximity sensors to be varied or steered; and
process the measurements from the proximity sensor to determine if the user has fallen.

* * * * *